US011971348B2

(12) United States Patent
Moon et al.

(10) Patent No.: US 11,971,348 B2
(45) Date of Patent: Apr. 30, 2024

(54) ELECTRONIC DEVICE AND METHOD OF ESTIMATING BIO-INFORMATION USING THE SAME

(71) Applicant: SAMSUNG ELECTRONICS CO., LTD., Suwon-si (KR)

(72) Inventors: Hyun Seok Moon, Hwaseong-si (KR); Yoon Jae Kim, Seoul (KR); Jin Young Park, Hwaseong-si (KR); Kun Sun Eom, Yongin-si (KR); Myoung Hoon Jung, Bucheon-si (KR); Jeong Eun Hwang, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 32 days.

(21) Appl. No.: 17/702,424

(22) Filed: Mar. 23, 2022

(65) Prior Publication Data
US 2023/0168188 A1 Jun. 1, 2023

(30) Foreign Application Priority Data

Nov. 29, 2021 (KR) ........................ 10-2021-0167629

(51) Int. Cl.
*G01N 21/31* (2006.01)
(52) U.S. Cl.
CPC . *G01N 21/314* (2013.01); *G01N 2201/06106* (2013.01)
(58) Field of Classification Search
CPC .......................... G01N 21/314; A61B 5/14551
See application file for complete search history.

(56) References Cited

U.S. PATENT DOCUMENTS

| | | | |
|---|---|---|---|
| 3,973,129 A * | 8/1976 | Blumberg | G01N 21/276 436/805 |
| 7,365,839 B2 | 4/2008 | Ferguson et al. | |
| 8,260,402 B2 | 9/2012 | Ermakov et al. | |
| 10,292,653 B2 | 5/2019 | Eom et al. | |

(Continued)

FOREIGN PATENT DOCUMENTS

| | | | | |
|---|---|---|---|---|
| CN | 104919289 A * | 9/2015 | | G01J 1/08 |
| KR | 10-1576461 B1 | 12/2015 | | |

(Continued)

OTHER PUBLICATIONS

Communication dated Oct. 12, 2022 issued by the European Patent Office in European Patent Application No. 22175823.8.

*Primary Examiner* — Maurice C Smith
(74) *Attorney, Agent, or Firm* — Sughrue Mion, PLLC

(57) ABSTRACT

An electronic device may include an optical sensor configured to emit a reference light to a reference object and detect the reference light reflected from the reference object during calibration, and emit a measurement light to a target object and detect the measurement light reflected from the target object during a measurement; and a processor configured to perform the calibration of the optical sensor while the electronic device is disposed to oppose or in contact with the reference object by controlling the optical sensor to emit and detect the reference light, and estimate bio-information based on a light quantity of the measurement light that is reflected from the target object by the optical sensor, and a light quantity of the reference light reflected from the reference object.

20 Claims, 16 Drawing Sheets

(56) References Cited

U.S. PATENT DOCUMENTS

| | | |
|---|---|---|
| 10,321,874 B2 | 6/2019 | Eom et al. |
| 10,585,467 B2* | 3/2020 | Moon ................ G01R 31/3835 |
| 10,849,513 B2* | 12/2020 | Shemesh ................ A61B 5/681 |
| 11,064,944 B2 | 7/2021 | Eom et al. |
| 11,150,183 B2* | 10/2021 | Eom ...................... G01N 21/49 |
| 11,234,647 B2* | 2/2022 | Kang ................ G06V 40/1306 |
| 2016/0112775 A1 | 4/2016 | Kim et al. |
| 2017/0209053 A1* | 7/2017 | Pantelopoulos ..... A61B 5/7264 |
| 2018/0024056 A1 | 1/2018 | Kim |
| 2019/0083034 A1* | 3/2019 | Shim ................. A61B 5/14551 |
| 2020/0029873 A1 | 1/2020 | Park et al. |
| 2020/0037956 A1 | 2/2020 | Kang et al. |
| 2020/0196935 A1 | 6/2020 | Eom et al. |
| 2021/0022677 A1 | 1/2021 | Kang et al. |
| 2021/0113087 A1* | 4/2021 | Jang .................. G01N 21/3151 |
| 2021/0330258 A1 | 10/2021 | Eom et al. |
| 2021/0356322 A1 | 11/2021 | Nam et al. |
| 2021/0404953 A1 | 12/2021 | Jung et al. |

FOREIGN PATENT DOCUMENTS

| | | |
|---|---|---|
| KR | 10-2016-0044811 A | 4/2016 |
| KR | 10-2016-0047844 A | 5/2016 |
| KR | 10-2020-0012597 A | 2/2020 |
| KR | 1020200012597 A | 2/2020 |
| KR | 10-2020-0077052 A | 6/2020 |
| KR | 10-2021-0047540 A | 4/2021 |

* cited by examiner

ELECTRONIC DEVICE AND METHOD OF ESTIMATING BIO-INFORMATION USING THE SAME

CROSS-REFERENCE TO RELATED APPLICATION(S)

This application claims priority from Korean Patent Application No. 10-2021-0167629, filed on Nov. 29, 2021, in the Korean Intellectual Property Office, the disclosure of which is incorporated herein by reference in their entirety.

BACKGROUND

1. Field

Apparatuses and methods consistent with example embodiments relate to estimating bio-information using an electronic device, and more particularly to non-invasively estimating antioxidant levels.

2. Description of the Related Art

Reactive oxygen species act as an important biological defense factor such as white blood cells protecting the body against infections. However, it has been known that excessive generation of reactive oxygen species in the body may lead to various tissue diseases. Common factors that cause the reactive oxygen species include stress, alcohol, peroxides, medicine, and the like. The reactive oxygen species produced by these factors may cause cranial nerve diseases, circulatory diseases, cancer, digestive tract diseases, liver diseases, arteriosclerosis, renal diseases, diabetes, aging, and the like. Our bodies have a series of antioxidant defense systems to protect against oxygen toxicity. For normal operation of the systems, it is essential to consume sufficient antioxidants such as vitamin E, vitamin C, carotenoid, flavonoid, and the like, and it is important to eat as many foods that are rich in antioxidants as possible for an effective antioxidant action. Accordingly, there is a need for an apparatus for easily identifying the amount of antioxidants in the body.

SUMMARY

According to an aspect of the present disclosure, there is provided an electronic device including: an optical sensor configured to emit a reference light to a reference object and detect the reference light reflected from the reference object during calibration, and emit a measurement light to a target object and detect the measurement light reflected from the target object during a measurement; and a processor configured to perform the calibration of the optical sensor while the electronic device is disposed to oppose or in contact with the reference object by controlling the optical sensor to emit and detect the reference light, and estimate bio-information based on a light quantity of the measurement light that is reflected from the target object by the optical sensor, and a light quantity of the reference light reflected from the reference object.

The sensor may include a light source configured to emit the reference light onto the reference object, and a detector configured to detect the reference light reflected from the reference object, wherein the processor may store, in a memory, calibration information including the light quantity of the reference light detected by the detector.

The electronic device may further include: an output device including either one or both of a haptic device and a speaker to output an output signal, the output signal including either one of both of a vibration signal and a sound signal, wherein the output device may be configured to output the output signal to guide the target object to press the optical sensor during a pressing phase of the measurement, stop outputting the output signal during a detection phase of the measurement in which the optical sensor detects the measurement light reflected from the target object, and output the output signal again during a completion phase of the measurement in which a detection of the measurement light is complete.

When the pressing phase begins, the output device may output the output signal with a predetermined intensity at least one or more times during the pressing phase, and then may gradually decrease an intensity of the output signal as pressure applied to the optical sensor increases, and in response to the pressure reaching a reference value, the output device may stop outputting the output signal.

During the pressing phase, in response to the pressure not reaching the reference value within a predetermined period of time, the output device may output the output signal in a different pattern from a pattern of the output signal which is output at a beginning of the pressing phase.

During the pressing phase, in response to pressure applied by the target object to the optical sensor reaching a reference value, the output device may output the output signal with a predetermined intensity at least one or more times.

The reference object may be disposed on a charger for charging the electronic device. When the electronic device is placed on the charger for charging and is in a charging state, the processor may automatically start to perform the calibration of the optical sensor.

The electronic device may further include a display configured to output a text that guides a user to estimate the bio-information when the electronic device is removed from the charger after the charging is complete or when a current time corresponds to a recommendation time based on a change in a user pattern.

The electronic device may further include a display configured to output a text or an image for guiding a user to place the target object on the optical sensor.

The processor may be further configured to determine a contact position when the target object comes into contact with the optical sensor. In response to the contact position not coinciding with a predetermined measurement position, an output device may output vibration or sound in a predetermined pattern.

The optical sensor may include a light source disposed at a center of the optical sensor, and a plurality of detectors disposed to surround the light source, wherein based on absorbances measured by each of the plurality of detectors, the processor may be further configured to determine the contact position of the target object.

The processor may be further configured to calculate absorbances at each wavelength based on the light quantity of the reference light measured from the reference object during the calibration, and the light quantity of the measurement light measured from the target object, obtain a feature value based on the calculated absorbances at each wavelength, and estimate the bio-information based on the obtained feature value.

The electronic device may further include a display configured to output a bio-information estimation result.

The processor may be further configured to combine the absorbances at each wavelength, obtain an antioxidant peak by correcting a baseline of a waveform of the absorbances, and obtain an antioxidant level based on the antioxidant peak by using a predefined antioxidant level estimation model.

According to another aspect of the present disclosure, there is provided a method of estimating bio-information by using an electronic device including an optical sensor. The method may include: performing calibration of the optical sensor by emitting a reference light to a reference object and detecting the reference light reflected from the reference object during calibration; guiding a user to follow measurement phases by outputting an output signal that includes either one or both of a vibration signal or a sound signal; measuring a light quantity of a measurement light that is emitted to and reflected from a target object; and estimating the bio-information based on the light quantity of the measurement light and a light quantity of the reference light reflected from the reference object.

The measurement phases may include a pressing phase, a detection phase, and a completion phase, and the guiding may include outputting the output signal during the pressing phase in which the target object to guide the user to press the optical sensor, stopping outputting the output signal during the detection phase in which the optical sensor detects the measurement light reflected from the target object, and outputting the output signal during the completion phase in which a detection of the measurement light is complete.

The guiding may include, when the pressing phase begins, outputting the output signal with a predetermined intensity at least one or more times during the pressing phase, and then gradually decreasing an intensity of the output signal as pressure applied to the optical sensor increases, and in response to the pressure reaching a reference value, stopping outputting the output signal.

The guiding may include, during the pressing phase, in response to pressure applied by the target object to the optical sensor reaching a reference value, outputting the output signal with a predetermined intensity at least one or more times.

The reference object may be disposed on a charger for charging the electronic device, wherein the performing of the calibration may include, automatically starting to perform the calibration when the electronic device is placed on the charger for charging and is in a charging state.

The estimating of the bio-information may include: calculating absorbances at each wavelength based on the light quantity of the reference light measured during the calibration and the light quantity of the measurement light measured from the target object; obtaining a feature value based on the calculated absorbances at each wavelength; and estimating the bio-information based on the obtained feature value.

BRIEF DESCRIPTION OF THE DRAWINGS

The above and/or other aspects will be more apparent by describing certain example embodiments, with reference to the accompanying drawings, in which.

DETAILED DESCRIPTION

Figure 1:
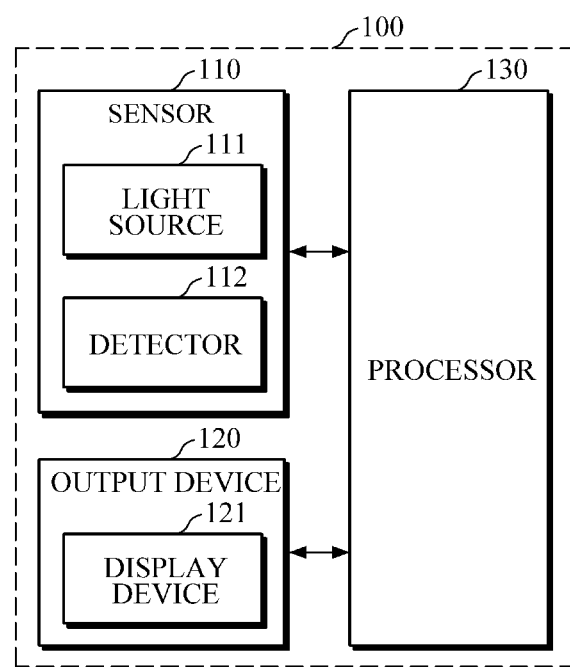
FIG. 1 is a block diagram illustrating an electronic device according to an example embodiment of the present disclosure.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'unit' or 'module', etc., should be understood as a unit that performs at least one function or operation and that may be embodied as hardware, software, or a combination thereof. Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

An electronic device according to various embodiments of the present disclosure which will be described below may include, for example, at least one of a wearable device, a smartphone, a tablet PC, a mobile phone, a video phone, an electronic book reader, a desktop computer, a laptop computer, a netbook computer, a workstation, a server, a PDA, a portable multimedia player (PMP), an MP3 player, a medical device, and a camera. The wearable device may include at least one of an accessory type wearable device (e.g., wristwatch, ring, bracelet, anklet, necklace, glasses, contact lens, or head mounted device (HMD)), a textile/clothing type wearable device (e.g., electronic clothing), a body-mounted type wearable device (e.g., skin pad or tattoo), and a body implantable type wearable device. However, the wearable device is not limited thereto and may include home appliances, such as a television, a digital video disk (DVD) player, a stereo system, a refrigerator, an air conditioner, a vacuum cleaner, an oven, a microwave oven, a washing machine, an air cleaner, a set-top box, a home automation control panel, a security control panel, a media box, a game console, an electronic dictionary, an electronic key, a camcorder, an electronic picture frame, etc., or may include various medical devices, for example, various portable medical measuring devices (blood glucose monitoring device, heart rate monitor, blood pressure measuring device, thermometer, etc.), magnetic resonance angiography (MRA), magnetic resonance imaging (MRI), computed tomography (CT), imaging system, ultrasonic system, etc.). However, the electronic device is not limited to the above devices.

FIG. 1 is a block diagram illustrating an electronic device according to an example embodiment of the present disclosure.

Referring to FIG. 1, an electronic device 100 includes a sensor 110, an output device 120, and a processor 130.

The sensor 110 may be disposed on a first surface (e.g., rear surface) of a main body of the electronic device 100, and may include a light source 111 and a detector 112. The sensor 110 may be implemented as any one or any combination of an optical health sensor, an antioxidant sensor, a blood glucose monitoring sensor, a triglyceride monitoring sensor, a blood alcohol detecting sensor, and a photoplethysmography (PPG) sensor. The light source 111 may include a light emitting diode (LED), a laser diode, a phosphor, and the like. There may be one or more light sources, each of which may emit light of different wavelengths (e.g., red wavelength, green wavelength, blue wavelength, infrared wavelength, etc.). For example, the light sources may emit light in a wavelength range of 400 nm to 600 nm.

The detector 112 may include a photodiode (PD), a phototransistor (PTr), a Complementary Metal Oxide Semiconductor (CMOS) image sensor, a charge-coupled device (CCD) image sensor, and the like. The detector 112 may be formed as a single detector, a plurality of detectors, or a detector array. The plurality of detectors or the detector array may be formed in a predetermined shape, for example, a concentric circle with the detectors being arranged around the outside of the light source 111, or in various shapes, such as a square, a triangle, and the like.

The output device 120 may visually or non-visually output data generated or processed by the electronic device 100. The output device 120 may include a display device 121 and a haptic/sound device 122.

The display device 121 may be disposed on a second surface (e.g., front surface) of the main body of the electronic device 100 and may visually provide information to the outside of the electronic device 100. The display device 121 may include, for example, a display, a hologram device, or a projector and control circuitry to control the devices. The display device 121 may include touch circuitry adapted to detect a touch, and/or sensor circuitry (e.g., force sensor, pressure sensor, etc.) adapted to measure the intensity of force incurred by the touch. In the following disclosure, the force sensor may also refer to the pressure sensor, and force measured by the force sensor may also refer to pressure. By contrast, the pressure sensor may also refer to the force sensor, and pressure measured by the pressure sensor may also refer to force.

A haptic/sound device 122 may be either a haptic device or a sound device. Alternatively, the haptic/sound device 122 may include both the haptic device and the sound device, in which case the respective devices may be provided as separate modules or may be integrally formed as one module.

The haptic module may convert an electrical signal into a mechanical stimulus (e.g., vibration, motion, etc.) or electrical stimulus which may be recognized by a user by tactile sensation or kinesthetic sensation. The haptic module may generate and apply forces, vibrations, or motions to a user. The haptic module may include, for example, a motor, a piezoelectric element, and/or an electric stimulator.

The sound device may output sound signals to the outside of the electronic device 100. The sound device may include a speaker, a receiver, and/or an audio module. The speaker may be used for general purposes, such as playing multimedia or playing record, and the receiver may be used for incoming calls. The receiver may be implemented separately from, or as part of, the speaker. The audio module may convert a sound into an electrical signal or vice versa. The audio module may obtain the sound via the input device, or may output the sound via the sound output device, and/or a speaker and/or a headphone of another electronic device directly or wirelessly connected to the electronic device.

The processor 130 may be electrically or wirelessly connected to various components of the electronic device 100, such as the sensor 110, the output device 120, etc., so as to control these components and to perform various data processing or computation.

For example, by controlling the sensor 110 and using light quantity data of light received by the detector 112 of the sensor 110, the processor 130 may perform calibration of the sensor 110 and/or may estimate bio-information. In particular, the bio-information may be antioxidant levels, including a concentration of carotenoid accumulated in skin. However, this is merely an example, and the bio-information may include a variety of information including blood glucose, triglyceride, alcohol, lactate, skin pigment, bloodstream amount, and the like.

First, the processor 130 may perform calibration of the sensor 110 using a reference object. In particular, the reference object may be a reflector (e.g., 100% reflection mirror, white reflector), or an object coated with a reflective material. The reflective material may be a diffuse reflection material having a reflectivity of 1% to 99%, and may be, for example, Barium sulfate (BaSO4), Teflon (PTFE), etc., but is not limited thereto.

For example, the reference object may be formed on one surface of a charger, i.e., a surface opposite to or coming into contact with the first surface of the main body when the main body of the electronic device 100 is placed on the charger. For example, when a user places the main body on the charger for charging the electronic device 100, the processor 130 may sense a charging state and may automatically start to perform calibration during charging. However, even in the charging state, the processor 130 may not perform calibration if calibration conditions are not satisfied, including a case where a predetermined calibration cycle is not started, or a case where a residual battery capacity until fully charged is less than or equal to a threshold (20%), and the like.

The processor 130 may drive the light source 111 of the sensor 110 to emit light onto the reference object of the charger, and may store a quantity of light, reflected from the reference object and detected by the detector 112, as a reference light quantity. The processor 130 may repeat or iterate this process a number of times, and may obtain a statistical value (e.g., an arithmetic mean value, a weighted mean value, a median value, a mode, a valley value, a peak value, etc.) of quantities of the reflected light, which are detected each number of times, as the reference light quantity of the light source. In addition, when the plurality of detectors 112 detect light quantities for each light source 111, the processor 130 may obtain a statistical value (e.g., an arithmetic mean value, a weighted mean value, a median value, a mode, a valley value, a peak value, etc.) of the light quantities detected by the respective detectors 112 as the reference light quantity of the corresponding light source.

In another example, the reference object may be a reflector, such as white paper, a holder with no charging function, etc., which may be easily used by a user, and in response to a user's request, the processor 130 perform calibration by using a user's reflector. In this case, reflectivity may vary depending on a type of the user's reflector, such that in order to correct the reflectivity, the processor 130 may perform primary calibration at the initial time of use of the user's reflector, at predetermined calibration intervals or in response to a user's request, by using the reference object formed on the charger, and then may perform secondary calibration by using the user's reflector and may correct the secondary calibration based on a result of the primary calibration.

Then, the processor 130 may determine a measurement state of the electronic device 100, and while providing a user with appropriate guide information for each stage through the output device 120 disposed on the second surface of the main body, the processor 130 may estimate bio-information by using the light quantity measured from the object (e.g., thumb) and the calibration result.

For example, if the electronic device 100 is in a state before estimating bio-information, the processor 130 may output visual information for guiding a user to estimate bio-information at a predetermined time of estimation recommendation. For example, when the electronic device 100 is placed on the charger and calibration is performed during charging, the processor 130 may output a text message, indicating estimation recommendation, at a time when the charging is complete or when the user removes the electronic device 100 from the charger to use the electronic device 100. In this case, the processor 130 may further output an estimation recommendation alarm by sound, vibrations, tactile sensation, etc., using the haptic/sound device 122 and the like of the output device 120.

Alternatively, by analyzing user patterns, such as a predetermined user preferred measurement time, a significant change in bio-information before a measurement time, or a change in life patterns, such as drinking, exercise, etc., the processor 130 may determine an estimation recommendation time, and upon determining that the estimation recommendation time has come, the processor 130 may output a text message, guiding a user to estimate bio-information, to the display device 121.

In response to a user's request for estimating bio-information, the processor 130 may guide the user to place an object on the sensor 110 through the display device 121. For example, the display device 121 may output a text, such as "please press the sensor 110 with your thumb," and/or may output an image of the thumb covering the sensor 110.

When the user places the object on the sensor 110, the haptic/sound device 122 may guide each measurement phase by interworking with the processor 130 to output different patterns of vibrations/sounds for each measurement phase. In particular, the patterns of vibrations/sounds may be defined as various patterns for each measurement phase based on, for example, an intensity of vibration/sound, a number of times of repeated outputs, a duration of each repeated output, and/or a time interval between the repeated outputs, and the like.

For example, in a contact phase in which the object comes into contact with the sensor 110, the processor 130 may determine a contact position between the object and the sensor 110, and the haptic/sound device 122 may guide a measurement position of the sensor 110 based on the determined contact position. In particular, the sensor 110 may include the light source 111 disposed at the center thereof, and the plurality of detectors 112 arranged around the outside of the light source 111, in which the processor 130 may calculate absorbance for each detector 112 based on quantities of light received by the respective detectors 112, and may determine a contact position of the object based on the absorbance.

For example, if the contact position of the object does not coincide with the measurement position of the sensor 110, the processor 130 may output vibration/sound in a first pattern. The processor 130 may repeat the process. If the contact position coincides with the measurement position or falls within a predetermined threshold range (e.g., a distance between the center of a touched fingerprint of the thumb and a center point of the measurement position (e.g., center point of the sensor) being less than or equal to a threshold value), the processor 130 may proceed to a measurement phase in which the sensor 110 measures light from the object.

However, the above process of determining the contact position of the object may be omitted depending on characteristics of the object, such as the case where the object fails to completely cover the entire surface of the sensor 110, or in response to a user's input. In this case, the processor 130 may proceed to a next phase of detecting light by using the detectors 112 being in contact with the object. If a contact region of the object does not satisfy a predetermined number of detectors 112 or does not cover a predetermined range (e.g., 70%) of the sensor 110, the processor 130 may guide the measurement position as described above.

When the object is in contact with the measurement position of the sensor 110, such that the sensor 110 measures light from the object, the haptic/sound device 122 may output predetermined patterns of vibrations/sounds for each of a pressing phase in which the object presses the sensor 110, a detection phase in which the sensor 110 detects light from the object, and a completion phase in which the light detection is complete.

First, the haptic/sound device 122 may output vibration/sound in a second pattern for the pressing phase. For example, at the beginning of the pressing phase, the haptic/sound device 122 may output vibration/sound with a predetermined intensity at least one or more times, and as pressure gradually increases by pressing, the haptic/sound device 122 may gradually decrease the intensity of the vibration/sound, and when the pressure reaches a reference value, the haptic/sound device 122 may stop outputting the vibration/sound. In another example, the haptic/sound device 122 may not output vibration/sound until pressure reaches the reference value when the object presses the sensor 110, and at a time when the pressure reaches the reference value, the haptic/sound device 122 may output the vibration/sound with a predetermined intensity at least one or more times, and then may stop outputting the vibration/sound. In yet another example, when the object presses the sensor 110 such that pressure gradually increases, the haptic/sound device 122 may gradually increase the vibration/sound within a range less than or equal to a first intensity, and at a time when the pressure reaches the reference value, the haptic/sound device 122 may output vibration/sound with a second intensity at least one or more times, and then may stop outputting the vibration/sound. However, the present disclosure is not limited to the above examples.

Then, when the pressure applied by the object to the sensor 110 reaches the reference value such that the haptic/sound device 122 enters into the detection phase, the haptic/ sound device 122 may output vibration/sound in a third pattern for a period of time (e.g., 5 seconds) when the sensor 110 detects light from the object. In this case, the third pattern may correspond to stopping the vibration/sound without outputting the vibration/sound. However, the present disclosure is not limited thereto. The sensor 110 may sequentially or simultaneously drive one or more light sources of different wavelengths in a range of 400 nm to 600 nm, and may detect light of the respective wavelengths using the detectors.

Subsequently, when the sensor 110 completes detection of light from the object, the haptic/sound device 122 may output vibration/sound in a fourth pattern. For example, the haptic/sound device 122 may output vibration/sound with a predetermined intensity at least one or more times. In this case, the second pattern and the fourth pattern may be different patterns, but are not limited thereto and may be set to the same pattern.

Next, when the sensor 110 completes detection of light scattered or reflected from the object, the processor 130 may calculate absorbances at each wavelength based on a ratio between a measured light quantity and a reference light quantity, may extract a feature value by using the absorbances at each wavelength. For example, the processor 130 may obtain a feature value by combining the calculated absorbances at each wavelength and by correcting a baseline of a waveform. The processor 130 may obtain bio-information by applying the obtained feature value to a predefined estimation model. The following Equations 1 to 3 represent an example of calculating absorbances at each wavelength and determining antioxidant levels by using absorbances at least at three wavelengths.

$$A(\lambda) = -\log_{10}\frac{I_m}{I_0} \qquad \text{[Equation 1]}$$

Herein, $A(\lambda)$ denotes the absorbance at each wavelength, $I_m$ denotes the measured light quantity, which is measured from the first portion of the object at a specific wavelength, and $I_0$ denotes the reference light quantity obtained by calibration at the specific wavelength.

$$AO = A_{\lambda 2} - \left(\frac{\lambda_3 - \lambda_2}{\lambda_3 - \lambda_1}\right) \times A_{\lambda 1} - \left(\frac{\lambda_2 - \lambda_1}{\lambda_3 - \lambda_1}\right) \times A_{\lambda 3} \qquad \text{[Equation 2]}$$

Herein, AO denotes, as an example of the feature value, an antioxidant peak obtained by combining the absorbances at each wavelength and correcting the baseline of the waveform; $\lambda_1$, $\lambda_2$, and $\lambda_3$ denote wavelengths; and $A_{\lambda 1}$, $A_{\lambda 2}$, and $A_{\lambda 3}$ denote the absorbances at each wavelength which are obtained using Equation 1, in which the wavelengths are relatively long in the order of $\lambda_1$, $\lambda_2$, and $A\lambda_3$.

$$Y = a \times AO + b \qquad \text{[Equation 3]}$$

Herein, Y denotes the antioxidant level, AO denotes the antioxidant peak, and a and b denote predetermined values. While Equation 3 denotes an antioxidant level estimation model which is defined as a linear function equation, the equation is not limited thereto and may be defined as a nonlinear function equation, such as a logarithmic function equation, an exponential function equation, and the like.

Then, the processor 130 may provide a bio-information estimation result to a user through the output device 120. For example, the processor 130 may display information, such as an estimated bio-information value, an estimation history graph, recommendations based on the estimated bio-information value, etc., and along with the information, the processor 130 may output alarm information by using the haptic/sound device 122 and the like.

Figure 2:
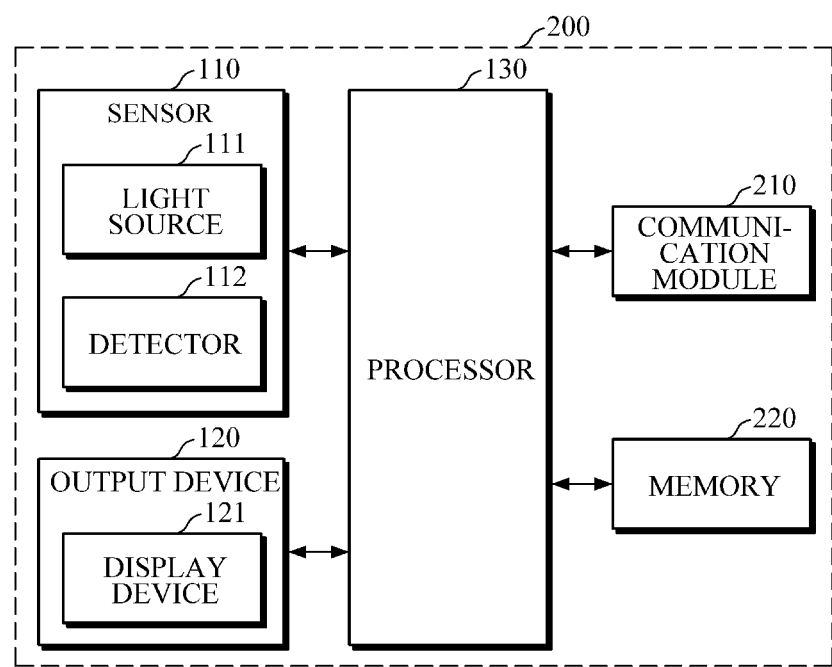
FIG. 2 is a block diagram illustrating an electronic device according to another example embodiment of the present disclosure.

FIG. 2 is a block diagram illustrating an electronic device according to another example embodiment of the present disclosure.

Referring to FIG. 2, an electronic device 200 includes the sensor 110, the output device 120, the processor 130, a communication module 210, and a memory 220. The sensor 110, the output device 120, and the processor 130 are described above, such that a detailed description thereof will be omitted.

The communication module 210 may support establishment of a direct (e.g., wired) communication channel and/or a wireless communication channel between the electronic device and other electronic device, a server, or the sensor device within a network environment, and performing of communication via the established communication channel. The communication module 210 may include one or more communication processors that are operable independently from the processor 130 and support a direct communication and/or a wireless communication. The communication module 210 may include a wireless communication module, e.g., a cellular communication module, a short-range wireless communication module, or a global navigation satellite system (GNSS) communication module, etc., and/or a wired communication module, e.g., a local area network (LAN) communication module, a power line communication (PLC) module, and the like. These various types of communication modules may be integrated into a single chip, or may be separately implemented as multiple chips. The wireless communication module may identify and authenticate the electronic device 200 in a communication network by using subscriber information (e.g., international mobile subscriber identity (IMSI), etc.) stored in a subscriber identification module.

For example, the communication module 210 may transmit necessary data so that an external device (e.g., smartphone, desktop PC) may output guide information for estimating bio-information at the same time when the output device 120 outputs guide information for estimating bio-information, and when the processor 120 completes estimation of bio-information, the communication module 210 may transmit a bio-information estimation result to the external device so that the estimation result may be output in various manners. Further, the communication module 210 may receive various data related to operation (e.g., estimation of bio-information) of the electronic device 200 from the external device.

The memory 220 may store operating conditions for operating the sensor 110, and various data required for other components of the electronic device. The various data may include, for example, software and input data and/or output data for a command related thereto. For example, the memory 220 may store, as calibration results (e.g., the reference light quantity $I_0$ obtained through calibration to be used in Equation 1), various data including the reference light quantity, the estimated bio-information value, the bio-information estimation model, and/or user characteristic information, such as a user's age, gender, health condition, and the like.

The memory 220 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

Hereinafter, various examples of guiding by the electronic devices 100 and 200 will be described with reference to FIGS. 3 to 8C.

Figure 3:
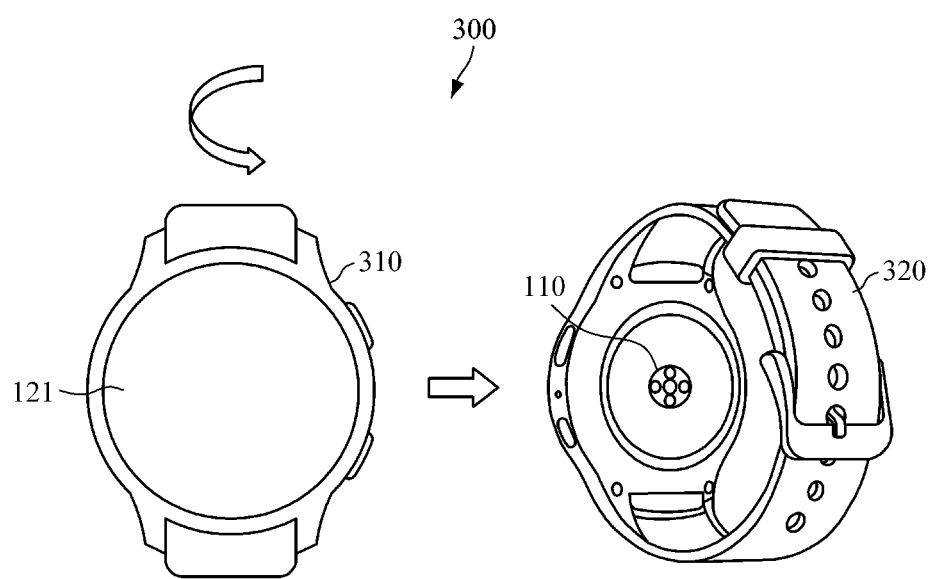
FIG. 3 is a diagram illustrating a smart watch wearable device according to an example embodiment of the present disclosure.

FIG. 3 is a diagram illustrating a smart watch wearable device as an example of the above electronic devices 100 and 200.

Referring to FIG. 3, the wearable device 300 includes a main body 310 and a strap 320. The main body 310 forms the exterior of the wearable device 300, and may have the display device 121 formed on a front surface thereof as illustrated herein, such that a variety of information including time information, received message information, bio-information estimation guide information, bio-information estimation results, and the like may be displayed thereon. Further, the sensor 110 may be disposed on a rear surface of the main body 310. A force sensor may be further disposed at a lower end of the sensor 110. The force sensor may measure a force applied when a user presses the sensor with a finger. If a force measured by the force sensor is equal to or greater than a reference value, the processor 130 mounted in the main body 310 may control the sensor 110 to proceed to the detection phase.

Figure 4:
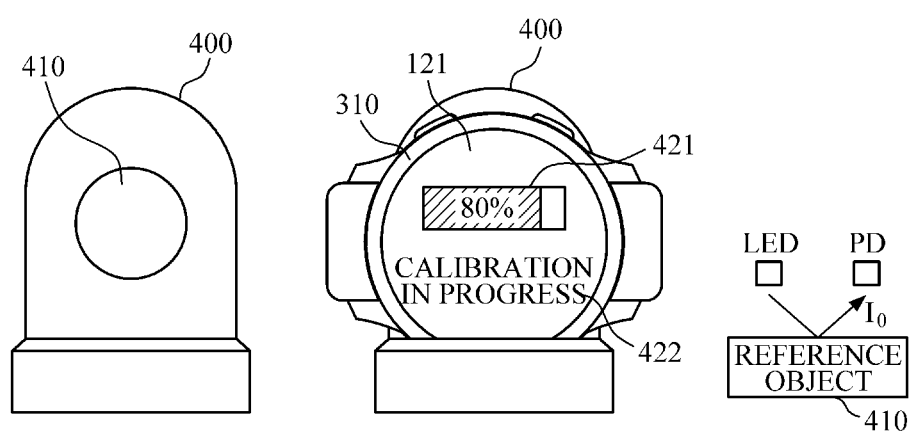
FIG. 4 is a diagram explaining an example of performing calibration of a sensor of an electronic device.

FIG. 4 is a diagram explaining an example of performing calibration of a sensor of an electronic device.

Referring to FIGS. 3 and 4, the smartwatch wearable device 300 may be placed on a charger 400 for wired or wireless charging. A reference object 410 may be disposed on the charger 400. As illustrated herein, the reference object 410 may be disposed at a position coming into contact with or opposite to the sensor 110, disposed on a rear surface of the main body 310, when the main body 310 of the wearable device 300 is placed on the charger 400. The reference object may be a reflector (e.g., reflection mirror, white reflector), or an object coated with a reflective material, for example, a diffuse reflection material having a reflectivity of 1% to 99%, and the diffuse reflection material may be, for example, Barium sulfate (BaSO4), Teflon (PTFE), and the like.

When the main body 310 of the wearable device 300 is placed on the charger 400, the processor 130 may automatically start to sense a charging state, and may output a status bar 421, indicating a charging level, to the display device 121. Further, while the wearable device 300 is in a charging state, the processor 130 may perform calibration of the sensor, and at the same time may display a text message 422, indicating that calibration is in progress, on the display device 422. For example, the processor 130 may control the sensor 110 to emit light onto the reference object and to detect light reflected from the reference object 410, and may store the detected light quantity as the reference light quantity $I_0$ in the memory 220.

Figure 5:
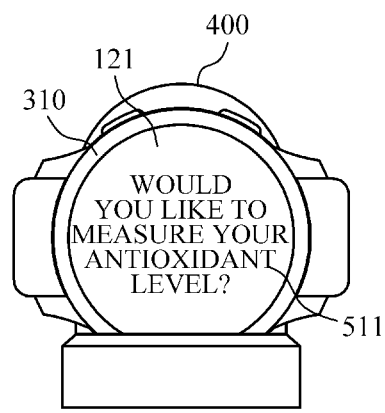
FIG. 5 is a diagram explaining an example of guiding estimation of bio-information.

FIG. 5 is a diagram explaining an example of guiding estimation of bio-information.

The processor 130 may determine a bio-information measurement state, and if the electronic device is in a state before measuring bio-information, the processor 130 may display information for recommending estimation of bio-information on the display device 121. For example, as illustrated herein, when charging is complete while the main body 310 is placed on the charger 400, the processor 130 may display a text message 511, such as "would you like to measure your antioxidant level?", on the display device 121. Alternatively, the processor 130 may output a message 511 for recommending estimation of bio-information at a time when a user removes the main body 310 from the charger 400 to use the wearable device 300 or at predetermined intervals. Alternatively, when a change in user pattern is detected, such as in the case where a user does intense exercise while wearing the wearable device 300 on the wrist or in the case where health-related data, including an antioxidant level, an alcohol level, blood pressure, blood glucose, triglyceride, and the like during a predetermined period, fall outside a predetermined range, the processor 130 may output a text message for recommending estimation of bio-information.

FIGS. 6A to 6D are diagrams explaining an example of guiding a measurement position of a bio-signal.

Figure 6A:
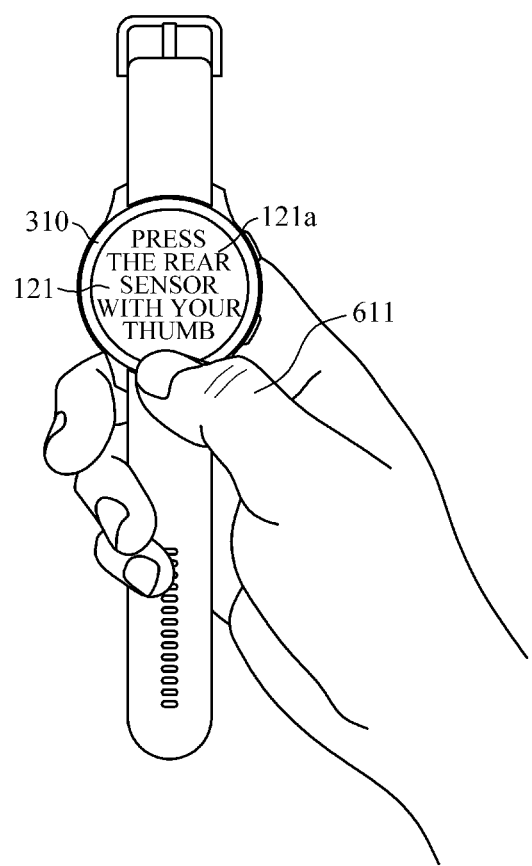
FIGS. 6A to 6D are diagrams explaining an example of guiding a measurement position of a bio-signal.
Figure 6B:
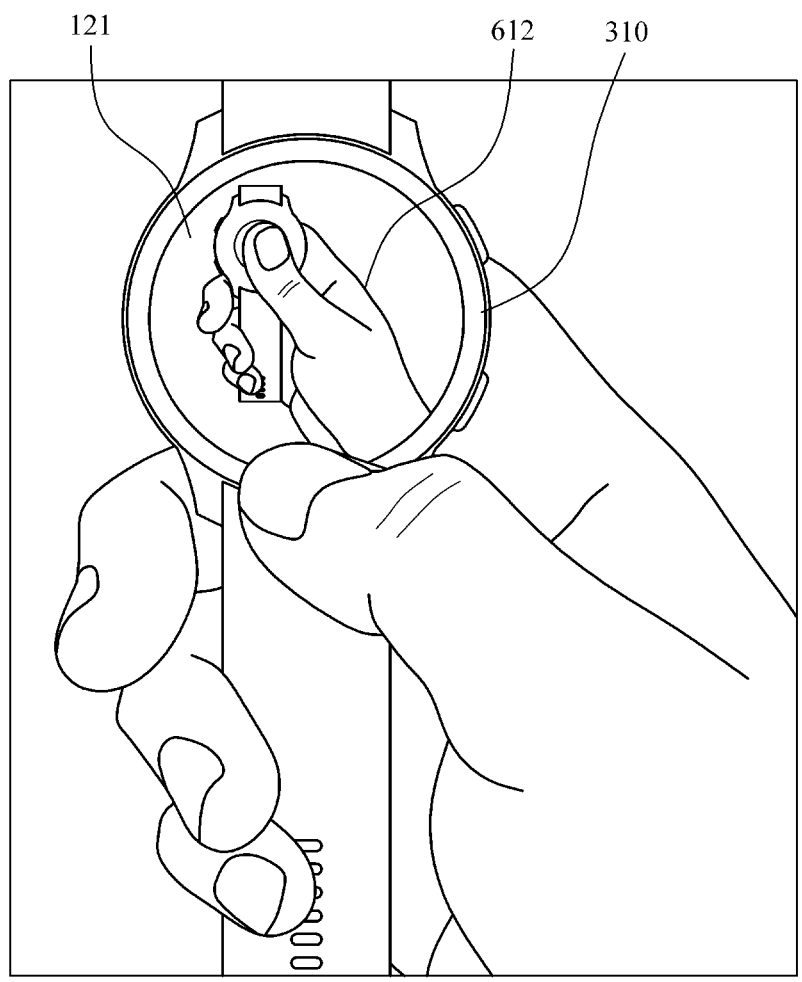

As illustrated in FIG. 6A, in response to a user's request for estimating bio-information, the display device 121 may output a text message 121a guiding the user to place, for example, a thumb 611 on the sensor 110 disposed on the rear surface of the main body 310. Alternatively, as illustrated in FIG. 6B, the display device 121 may display an image 612 of the thumb placed on the sensor disposed on the rear surface of the main body 310.

Figure 6C:
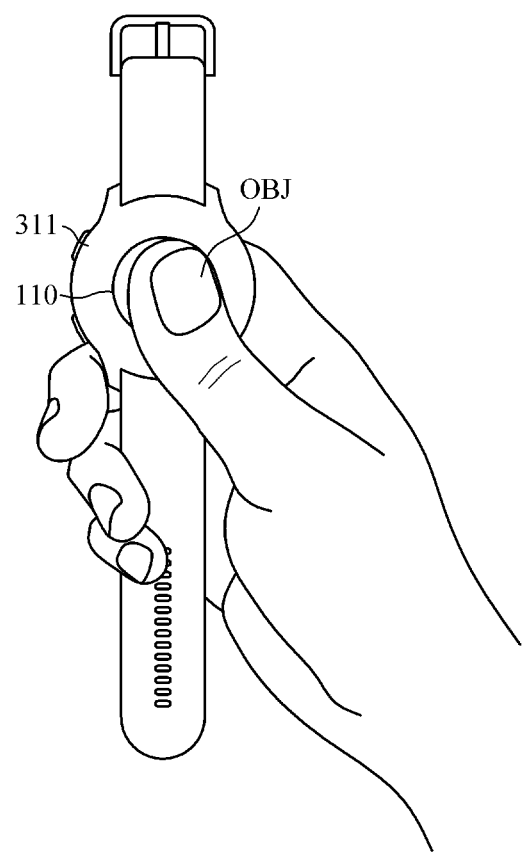
Figure 6D:
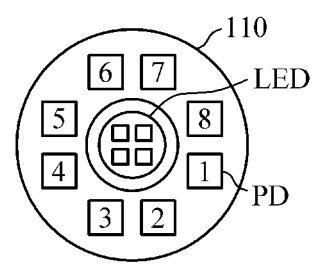

Referring to FIG. 6C, the user may flip over the main body and place the thumb OBJ on the sensor 110 disposed on a rear surface 311 of the main body. In particular, as illustrated in FIG. 6D, the sensor 110 may include one or more light sources LED disposed at the center thereof, and a plurality of detectors PD arranged in a concentric circle around the outside of the light sources LED. When the thumb is placed on the sensor 110, the processor 130 may calculate absorbances for the respective detectors PD by using the quantities of light detected by the respective detectors PD as shown in the above Equation 1, and may determine the contact position based on the calculated absorbances. In this case, if the contact position of the object does not coincide with the measurement position of the sensor 110, the haptic/sound device 122 may output predetermined patterns of vibrations/sounds, as will be described below with reference to FIG. 7A.

Figure 7A:
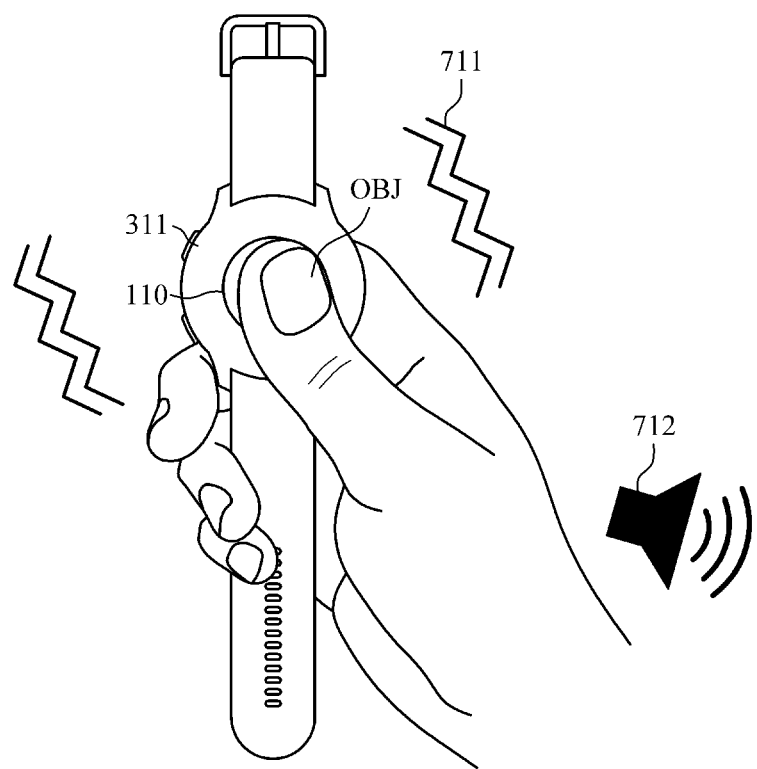
FIGS. 7A to 7C are diagrams explaining an example of guiding measurement phases.
Figure 7B:
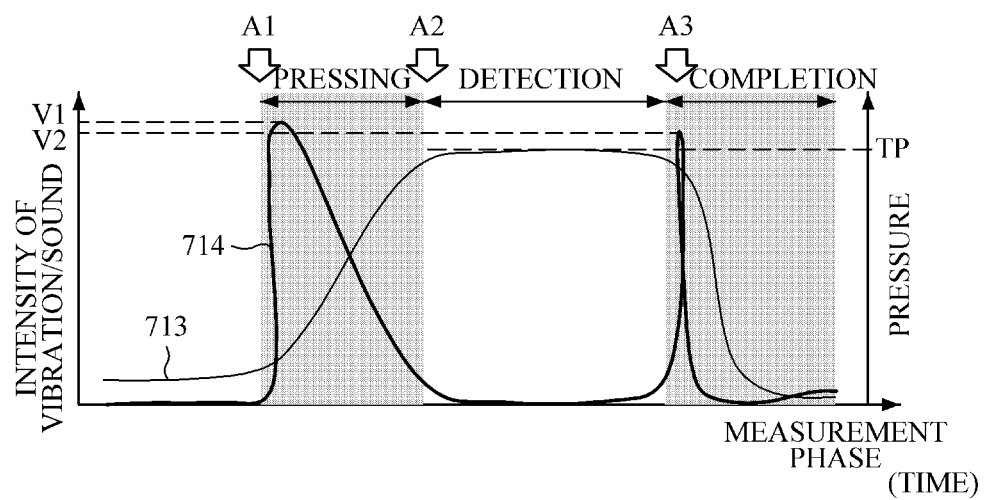
Figure 7C:
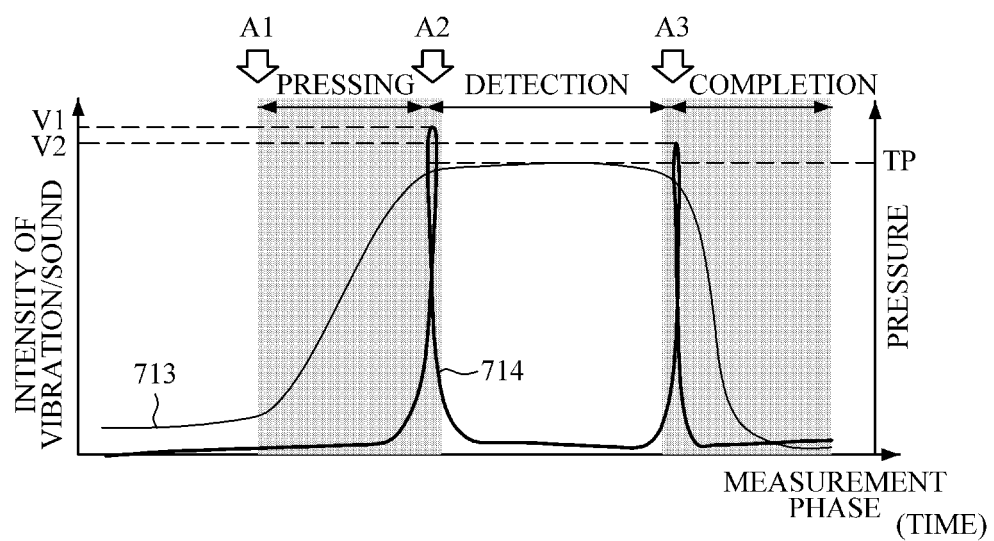

FIGS. 7A to 7C are diagrams explaining an example of guiding measurement phases.

Referring to FIGS. 7A to 7C, while the object OBJ is in contact with the sensor 110 disposed on the rear surface 311 of the main body, the haptic/sound device 122 may output vibration 711 and/or sound 712 for guiding each measurement phase when each of a plurality of measurement phases (e.g., a pressing phase, a detection phase, a completion phase) is performed.

For example, as illustrated in FIG. 7B, vibration/sound 714 is output with a first intensity V1 at a time A1 when pressurization 713 begins, and then gradually decreases with an increase in pressurization 713, and may be stopped at a time A2 when the pressurization 713 reaches a reference value TP. Then, detection of light is performed while the output of the vibration/sound 714 remains stopped, and at a time A3 when the light detection is complete, the vibration/sound 714 may be output again with a second intensity V2. In this case, the first intensity and the second intensity may be different from or equal to each other.

In another example, as illustrated in FIG. 7C, the vibration/sound 714 is not output during a period from the time point A1 when the pressurization 713 begins until the pressurization 713 reaches the reference value TP, and at a time A2 when the pressurization 713 reaches the reference value TP, the vibration/sound 714 may be output with the first intensity V1. Then, detection of light is performed while the output of the vibration/sound 714 remains stopped, and at the time A3 when the light detection is complete, the vibration/sound 714 may be output again with the second intensity V2. In this case, the first intensity and the second intensity may be different from or equal to each other.

Figure 8A:
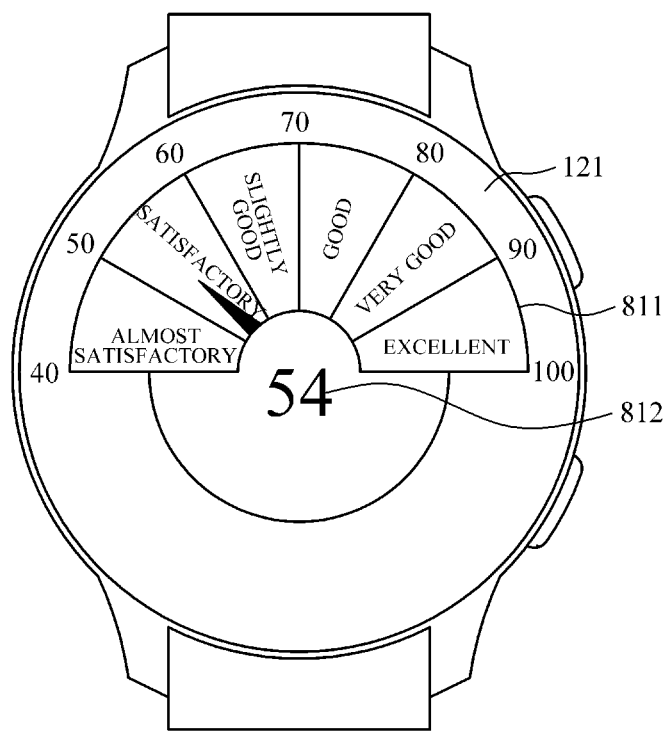
FIGS. 8A to 8C are diagrams explaining an example of outputting a bio-information estimation result.
Figure 8B:
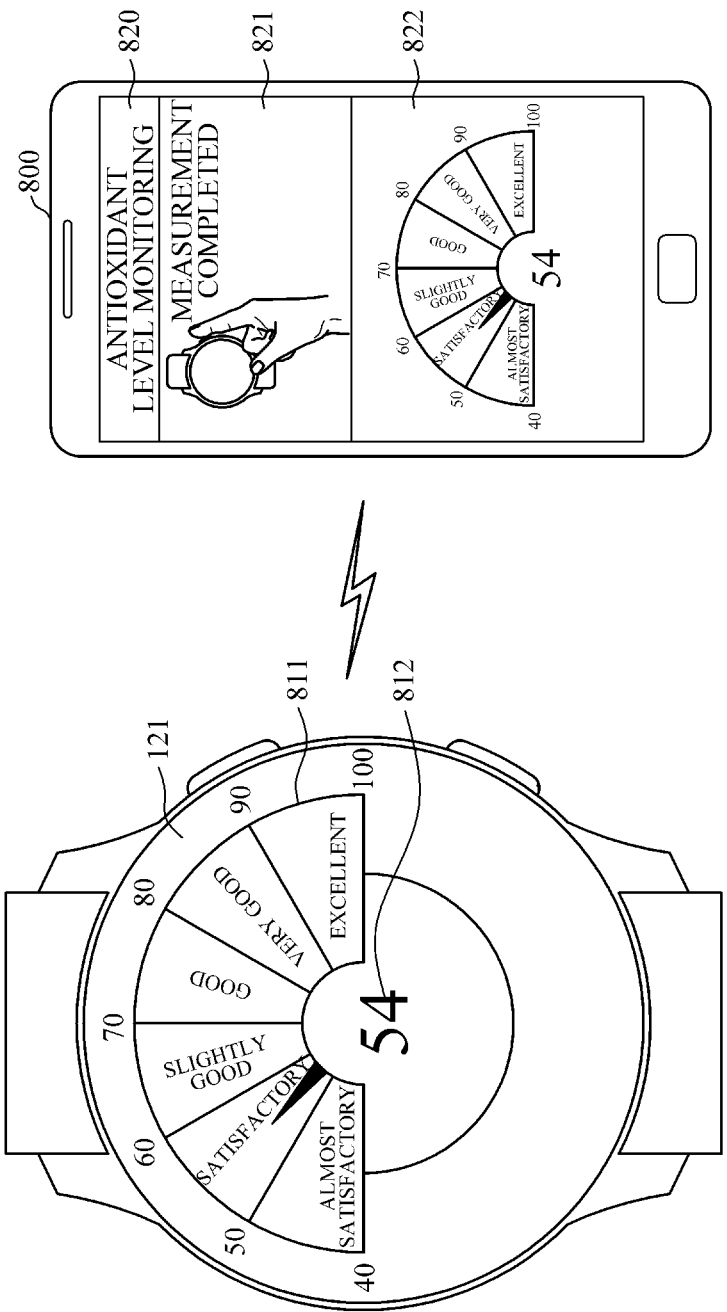
Figure 8C:
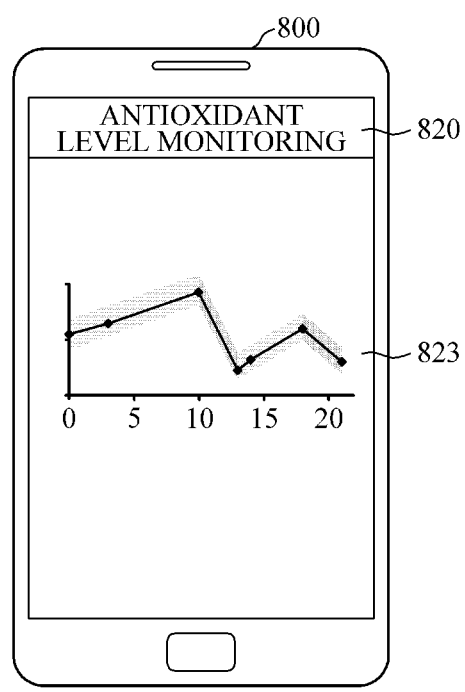

FIGS. 8A to 8C are diagrams explaining an example of outputting a bio-information estimation result.

Once light is detected from the object, the processor 130 may obtain, for example, an antioxidant level, by using the reference light quantity which is obtained based on the measured light quantity and by calibration as described above with reference to Equations 1 to 3, and may display the antioxidant level on the display device 121 by using various visual methods, such as a circular chart 811 and/or a text 812 indicating the antioxidant level as illustrated in FIG. 8A, so that a user may easily recognize an estimation result. The processor 130 may estimate the antioxidant level of an object in real time, or at the same time while the sensor 110 is collecting an optical signal from the object.

Further, referring to FIG. 8B, while estimating the antioxidant level and/or when completing estimation of bio-information, the processor 130 may transmit data regarding a progress and/or an estimation result to an external device 800 through the communication module, and the external device 800 may display a graphic object 821 indicating progress and/or a graphic object 822 indicating an estimation result on the display device 820. In addition, referring to FIG. 8C, the external device 800 may manage results received from the wearable device, and in response to a user's request, the external device 800 may visually display an antioxidant level estimation history in a graph 823.

Figure 9:
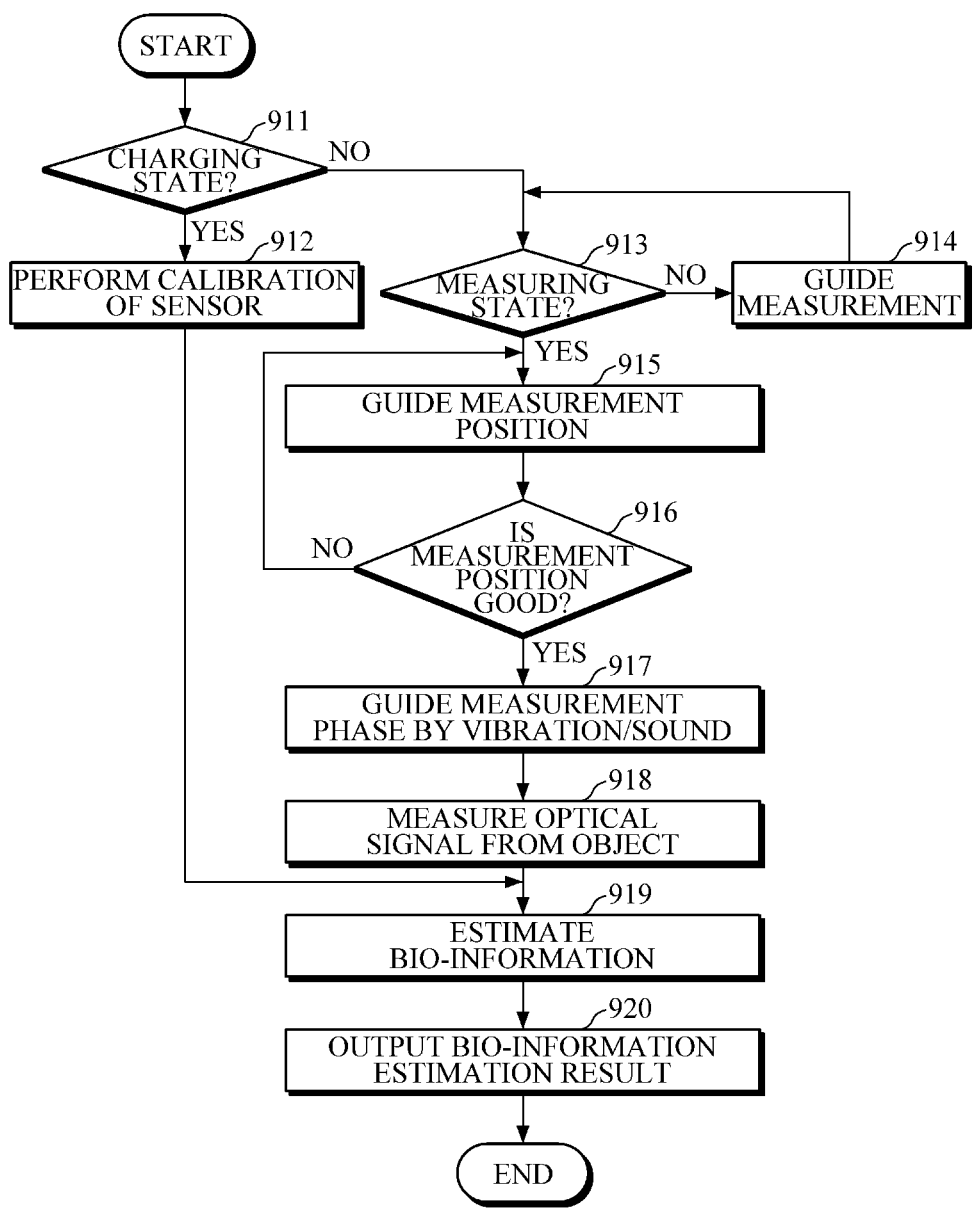
FIG. 9 is a flowchart illustrating a method of estimating bio-information according to an example embodiment of the present disclosure.

FIG. 9 is a flowchart illustrating a method of estimating bio-information according to an example embodiment of the present disclosure.

The method of FIG. 9 is an example of a method of estimating bio-information performed by the electronic devices 100 and 200 of FIGS. 1 and 2, which will be briefly described below in order to avoid redundancy.

First, the electronic device may determine whether the electronic device is in a charging state in operation 911.

Then, when the electronic device is placed on, for example, the charger and charging is started, the electronic device may perform calibration of the sensor by emitting light to a reference object disposed on the charger and then collecting the light reflected from the reference object, in operation 912. During the calibration, the electronic device may measure a reference light quantity of each light source based on the light reflected from the reference object, and may store the reference light quantity in the memory to be used in operation 919.

Subsequently, the electronic device may determine whether the electronic device is in a measurement state for measuring bio-information in operation 913, and if the electronic device is not in the measurement state, the electronic device may guide a user to measure bio-information in operation 914. For example, when charging is complete after the electronic device is placed on the charger and calibration is performed, or when a user removes the electronic device from the charger to use the electronic device, the electronic device may output a text message, indicating estimation recommendation, on the display device of the electronic device. Alternatively, by analyzing a predetermined user preferred measurement time or a change in user pattern, the electronic device may determine a time of estimation recommendation. Further, in response to a user's request for estimating bio-information, the electronic device may output a text message, guiding a user to place the object on the sensor, to the display device.

Next, when the electronic device is in the measurement state in operation 913 when the user places the object on the sensor for estimating bio-information, the electronic device may guide the user on a measurement position in operation 915. For example, the electronic device may determine a contact position of the object being in contact with the sensor, and may guide the user on the measurement position of the sensor through the haptic/sound device. In this case, based on a difference in quantities of light received by the plurality of detectors, the electronic device may determine the contact position, and may repeat the process until the contact position coincides with the measurement position. For example, the electronic device may determine that the contact position is good when a coincidence range between the contact position and the measurement position falls within a predetermined threshold range (e.g., when a distance between the center of a thumb placed on a contact surface of the sensor 110, and the center of the contact surface of the sensor 110, is less than or equal to a threshold value).

Then, when the contact position is determined to be good in operation 916, the electronic device may guide the user on measurement phases in operation 917. For example, after the object comes into contact with the measurement position, the haptic/sound device may guide each of the measurement phases by outputting vibrations/sound according to patterns for each of the pressing phase, detection phase, and completion phase.

Subsequently, when the contact pressure reaches a reference value, the sensor may measure an optical signal from the object in operation 918.

Next, the electronic device may estimate bio-information in operation 919 by using the light quantity measured in operation 918 and the reference light quantity obtained in operation 912. For example, the electronic device may calculate absorbances at each wavelength based on a ratio between the measured light quantity and the reference light quantity, may extract a feature value by using the absorbances at each wavelength, and may obtain bio-information by applying the obtained feature value to a predefined estimation model.

Then, the electronic device may provide the user with a bio-information estimation result through the output device in operation 920. For example, the electronic device may display information, such as an estimated bio-information value, an estimation history graph, recommendations based on the estimated bio-information value, and the like, on the display device and along with the information, the electronic device may provide alarm information by using a sound output device, a haptic device, etc., and may transmit result data and the like to an external device so that the external device may output the data.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An electronic device comprising:
an optical sensor configured to emit a reference light to a reference object disposed on a charger and detect the reference light reflected from the reference object during calibration which occurs while a battery of the electronic device is being charged, and emit a measurement light to a target object and detect the measurement light reflected from the target object during a measurement; and
a processor configured to, during a battery charging state of the electronic device, perform the calibration of the optical sensor while the electronic device is disposed to oppose or in contact with the reference object by controlling the optical sensor to emit to the reference object and detect the reference light, and after the battery charging state, estimate bio-information based on a light quantity of the measurement light that is reflected from the target object by the optical sensor, and a light quantity of the reference light reflected from the reference object.

2. The electronic device of claim 1, wherein the sensor comprises a light source configured to emit the reference light onto the reference object, and a detector configured to detect the reference light reflected from the reference object,
wherein the processor stores, in a memory, calibration information including the light quantity of the reference light detected by the detector.

3. The electronic device of claim 1, further comprising:
an output device comprising either one or both of a haptic device and a speaker to output an output signal, the output signal comprising either one of both of a vibration signal and a sound signal,
wherein the output device is configured to output the output signal to guide the target object to press the optical sensor during a pressing phase of the measurement, stop outputting the output signal during a detection phase of the measurement in which the optical sensor detects the measurement light reflected from the target object, and output the output signal again during a completion phase of the measurement in which a detection of the measurement light is complete.

4. The electronic device of claim 3, wherein when the pressing phase begins, the output device outputs the output signal with a predetermined intensity at least one or more times during the pressing phase, and then gradually decreases an intensity of the output signal as pressure applied to the optical sensor increases, and in response to the pressure reaching a reference value, the output device stops outputting the output signal.

5. The electronic device of claim 4, wherein during the pressing phase, in response to the pressure not reaching the reference value within a predetermined period of time, the output device outputs the output signal in a different pattern from a pattern of the output signal which is output at a beginning of the pressing phase.

6. The electronic device of claim 3, wherein during the pressing phase, in response to pressure applied by the target object to the optical sensor reaching a reference value, the output device outputs the output signal with a predetermined intensity at least one or more times.

7. The electronic device of claim 1,
wherein when the electronic device is in the battery charging state, the processor automatically starts to perform the calibration of the optical sensor.

8. The electronic device of claim 7, further comprising a display configured to output a text that guides a user to estimate the bio-information when the electronic device is removed from the charger after the charging is complete or when a current time corresponds to a recommendation time based on a change in a user pattern.

9. The electronic device of claim 1, further comprising a display configured to output a text or an image for guiding a user to place the target object on the optical sensor.

10. The electronic device of claim 1, wherein the processor is further configured to determine a contact position when the target object comes into contact with the optical sensor,
wherein in response to the contact position not coinciding with a predetermined measurement position, an output device outputs vibration or sound in a predetermined pattern.

11. The electronic device of claim 10, wherein the optical sensor comprises a light source disposed at a center of the optical sensor, and a plurality of detectors disposed to surround the light source,
wherein based on absorbances measured by each of the plurality of detectors, the processor is further configured to determine the contact position of the target object.

12. The electronic device of claim 1, wherein the processor is further configured to calculate absorbances at each wavelength based on the light quantity of the reference light measured from the reference object during the calibration, and the light quantity of the measurement light measured from the target object, obtain a feature value based on the calculated absorbances at each wavelength, and estimate the bio-information based on the obtained feature value.

13. The electronic device of claim 1, further comprising a display configured to output a bio-information estimation result.

14. The electronic device of claim 12, wherein the processor is further configured to combine the absorbances at each wavelength, obtain an antioxidant peak by correcting a baseline of a waveform of the absorbances, and obtain an antioxidant level based on the antioxidant peak by using a predefined antioxidant level estimation model.

15. A method of estimating bio-information by using an electronic device comprising an optical sensor, the method comprising:
performing calibration of the optical sensor by emitting a reference light to a reference object disposed on a charger and detecting the reference light reflected from the reference object during calibration which occurs while a battery of the electronic device is being charged;
after a battery charging state of the electronic device, guiding a user to follow measurement phases by outputting an output signal that comprises either one or both of a vibration signal or a sound signal;
measuring a light quantity of a measurement light that is emitted to and reflected from a target object; and
estimating the bio-information based on the light quantity of the measurement light and a light quantity of the reference light reflected from the reference object.

16. The method of claim 15, wherein the measurement phases comprises a pressing phase, a detection phase, and a completion phase, and
wherein the guiding comprises outputting the output signal during the pressing phase in which the target object to guide the user to press the optical sensor, stopping outputting the output signal during the detection phase in which the optical sensor detects the measurement light reflected from the target object, and outputting the output signal during the completion phase in which a detection of the measurement light is complete.

17. The method of claim 16, wherein the guiding comprises, when the pressing phase begins, outputting the output signal with a predetermined intensity at least one or more times during the pressing phase, and then gradually decreasing an intensity of the output signal as pressure applied to the optical sensor increases, and in response to the pressure reaching a reference value, stopping outputting the output signal.

18. The method of claim 16, wherein the guiding comprises, during the pressing phase, in response to pressure applied by the target object to the optical sensor reaching a reference value, outputting the output signal with a predetermined intensity at least one or more times.

19. The method of claim 15,
wherein the performing of the calibration comprises, automatically starting to perform the calibration when the electronic device is in the battery charging state.

20. The method of claim 15, wherein the estimating of the bio-information comprises:
calculating absorbances at each wavelength based on the light quantity of the reference light measured during the calibration and the light quantity of the measurement light measured from the target object;
obtaining a feature value based on the calculated absorbances at each wavelength; and
estimating the bio-information based on the obtained feature value.

* * * * *